United States Patent [19]

deSolms et al.

[11] Patent Number: 5,703,241
[45] Date of Patent: Dec. 30, 1997

[54] INHIBITOR OF FARNESYL-PROTEIN TRANSFERASE

[75] Inventors: S. Jane deSolms, Norristown; Samuel L. Graham, Schwenksville, both of Pa.

[73] Assignee: Merck & Co., Inc., Rahway, N.J.

[21] Appl. No.: 729,265

[22] Filed: Oct. 10, 1996

[51] Int. Cl.$^6$ ............... A61K 31/415; C07D 403/02
[52] U.S. Cl. ..................... 548/314.7; 514/397
[58] Field of Search ............ 548/314.7; 514/397

[56] References Cited

U.S. PATENT DOCUMENTS

| | | | |
|---|---|---|---|
| 5,043,268 | 8/1991 | Stock | 435/15 |
| 5,055,467 | 10/1991 | Albaugh | 514/235.8 |
| 5,141,851 | 8/1992 | Brown et al. | 435/15 |
| 5,151,497 | 9/1992 | Uchida et al. | 530/331 |
| 5,238,922 | 8/1993 | Graham et al. | 514/18 |
| 5,326,773 | 7/1994 | Desolms et al. | 514/336 |
| 5,340,828 | 8/1994 | Graham et al. | 514/357 |
| 5,352,705 | 10/1994 | Deana | 514/630 |
| 5,420,245 | 5/1995 | Brown et al. | 530/328 |
| 5,504,212 | 4/1996 | Desolms et al. | 546/336 |

FOREIGN PATENT DOCUMENTS

| | | |
|---|---|---|
| 0 456 180 A1 | 11/1991 | European Pat. Off. . |
| 0 618 221 A2 | 10/1994 | European Pat. Off. . |
| 0 675 112 A1 | 10/1995 | European Pat. Off. . |
| H7-112930 | 5/1995 | Japan . |
| 2 130 590 | 6/1984 | United Kingdom . |
| WO 91/16340 | 10/1991 | WIPO . |
| WO 94/09766 | 5/1994 | WIPO . |
| WO 94/10138 | 5/1994 | WIPO . |
| WO 95/09000 | 4/1995 | WIPO . |
| WO 95/09001 | 4/1995 | WIPO . |
| WO 95/11917 | 5/1995 | WIPO . |
| WO 96/31525 | 10/1996 | WIPO . |
| WO 96/34010 | 10/1996 | WIPO . |

OTHER PUBLICATIONS

Bos, Johannes L., "ras Oncogenes in Human Cancer: A Review," Cancer Research, vol. 49, pp. 4682–4689 (1989).
Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).
Goldstein, J.L. et al., "Nonfarnesylated Tetrapeptide Inhibitors of Protein Farnesyltransferase," The Journal of Biological Chemistry, vol. 266, No. 24, pp. 15575–15578 (1991).
James, G.L. et al., "Benzodiazepine Peptidomimetic BZA–5B Interrupts the MAP Kinase Activation Pathway in H–Ras–transformed Rat–1 Cells, but Not in Untransformed Cells," The Journal of Biological Chemistry, vol. 269, No. 44, pp. 27705–27714 (1994).
James, G.L. et al., "Benzodiazepine Peptidomimetics: Potent Inhibitors of Ras Farnesylation in Animal Cells", Science, vol. 260, pp. 1937–1942 (1993).

James, G., et al., "Polylysine and CVIM Sequences of K–RasB Dictate Specificity of Prenylation and Confer Resistance to Benzodiazepine Peptidomimetic in Vitro," The Journal of Biological Chemistry, vol. 270, No. 11, pp. 6221–626 (1995).
Kohl, N.E., et al., "Inhibition of farnesyltransferase induces regression of mammary and salivary carcinomas in ras transgenic mice," Nature Medicine, vol. 1, No. 8, pp. 792–797 (1995).
Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).
Kohl, N.E. et al., "Selective Inhibition of ras–Dependent Transformation by a Farnesyltransferase Inhibitor", Science, vol. 260, pp. 1934–1937 (1993).
Omura, S. et al., "Pepticinnamins, New Farnesyl–Protein Transferase Inhibitors Produced by an Actinomycete," The Journal of Antibiotics, vol. 46, No. 2, pp. 222–228 (1993).
Pompliano, D.L., et al., "Steady–State Kinetic Mechanism of Ras Farnesyl:Protein Transferase", Biochemistry, vol. 31, pp. 3800–3807 (1992).
Sebolt–Leopold, J.S. et al., "Inhibition of ras farnesyltransferase by a novel class of peptides containing no cysteine or thiol moieties," Proc. Am. Assoc. Cancer Res., vol. 35, p. 593 (1994).
Sepp–Lorenzino, L., et al., "A Peptidomimetic Inhibitor of Farnesyl:Protein Transferase Blocks the Anchorage–dependent and–independent Growth of Human Tumor Cell Lines," Cancer Research, vol. 55, pp. 5302–5309 (1995).
Shiomi, K., et al., "Pepticinnamins, New Farnesyl–Protein Transferase Inhibitors Produced by an Actinomycete," The Journal of Antiobiotics, vol. 46, No. 2, pp. 229–234 (1993).

*Primary Examiner*—Floyd D. Higel
*Attorney, Agent, or Firm*—David A. Muthard; Mark R. Daniel

[57] ABSTRACT

The present invention comprises an analog of the $CA_1A_2X$ motif of the protein Ras that is modified by farnesylation in vivo. This $CA_1A_2X$ analog inhibits the farnesyl-protein transferase and the farnesylation of certain proteins. Furthermore, this $CA_1A_2X$ analog differs from most compounds previously described as inhibitors of farnesyl-protein transferase in that it does not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. The compound of the instant invention also incorporates a cyclic amine moiety in the $A^1$ position of the motif. Further contained in this invention are chemotherapeutic compositions containing this farnesyl transferase inhibitor and methods for its production.

4 Claims, No Drawings

INHIBITOR OF FARNESYL-PROTEIN TRANSFERASE

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, Ann. Rev. Biochem. 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$_1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., Science, 260:1934–1937 (1993) and G. L. James et al., Science, 260:1937–1942 (1993)). Recently, it has been shown that an inhibitor of farnesyl-protein transferase blocks the growth of ras-dependent tumors in nude mice (N. E. Kohl et al., Proc. Natl. Acad. Sci U.S.A., 91:9141–9145 (1994) and induces regression of mammary and salivary carcinomas in ras transgenic mice (N. E. Kohl et al., Nature Medicine, 1:792–797 (1995).

It has recently been shown that farnesyl-protein transferase inhibitors are inhibitors of proliferation of vascular smooth muscle cells and are therefore useful in the prevention and thereapy of arteriosclerosis and diabetic disturbance of blood vessels (JP H7-112930).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable. A limited number of non-thiol FPTase inhibitors that are competitive with the Ras substrate have been described. These include a group of antibiotics known as the pepticinnamins (Omura, et al., J. Antibiotics 46:222 (1993)), and some non-thiol peptidyl analogs (WO 95/09000-A1, WO 95/09001-A1 and EP 0 675 122-A1).

It is, therefore, an object of this invention to develop a tetrapeptide-based compound that does not have a thiol moiety, and that will inhibit farnesyl-protein transferase and thus, the post-translational farnesylation of proteins. It is further the object of this invention to develop an inhibitor of farnesyl-protein transferase that exhibits sustained inhibition of FPTase in vivo following a single dose. It is also an object of this invention to develop chemotherapeutic compositions containing the compound of this invention and methods for producing the compound of this invention.

SUMMARY OF THE INVENTION

The present invention comprises an analog of the $CA^1A^2X$ motif of the protein Ras that is modified by farnesylation in vivo. This $CA^1A^2X$ analog inhibits farnesyl-protein transferase. Furthermore, this $CA^1A^2X$ analog differs from most analogs previously described as inhibitors of farnesyl-protein transferase (FPTase) in that it does not have a thiol moiety. The lack of the thiol offers unique advantages in terms of improved pharmacokinetic behavior in animals, prevention of thiol-dependent dependent chemical reactions, such as rapid autoxidation and disulfide formation with endogenous thiols, and reduced systemic toxicity. The particular compound of the instant invention also incorporates a cyclic amine moiety in the A[1] position of the motif. This particular compound exhibits unexpected sustained inhibition of FPTase in white blood cells of mammals following a single administration of the compound. Such sustained inhibition in white blood cells is indicative of sustained inhibition of farnesyl-protein transferase by the instant compound in the target tissues. Further contained in this invention are chemotherapeutic compositions containing this farnesyl-protein transferase inhibitor and methods for its production.

The compound of this invention is illustrated by the formula:

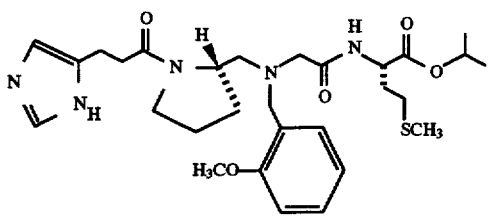

DETAILED DESCRIPTION OF THE INVENTION

The compound of this invention inhibits the farnesyl-protein transferase in vivo and is illustrated by the formula:

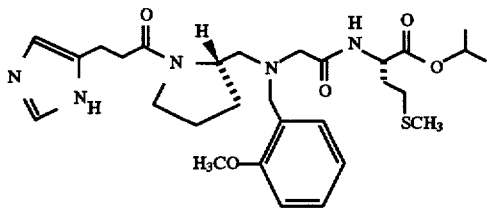

or a pharmaceutically acceptable salt thereof.

The compound of the instant invention is the prodrug form of a compound having a free carboxylic acid in place of the isopropyl ester of the instant compound and which has demonstrated inhibitory activity against farnesyl protein transferase in vitro. The synthesis of the acid form of the compound of the instant invention is shown in Example 2.

The compound of the present invention may have asymmetric centers and occur as racemates, racemic mixtures, and as individual diastereomers, with all possible isomers, including optical isomers, being included in the present invention. Unless otherwise specified, named amino acids are understood to have the natural "L" stereoconfiguration.

The pharmaceutically acceptable salts of the compound of this invention include the conventional non-toxic salts of the compound of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, benzenesulfonic, toluenesulfonic, methanesulfonic, ethane disulfonic, oxalic, isethionic, trifluoroacetic and the like.

The pharmaceutically acceptable salts of the compound of this invention can be synthesized from the compound of this invention, which contains a basic moiety by conventional chemical methods. Generally, the salts are prepared by ion exchange chromatography or by reacting the free base with stoichiometric amounts or with an excess of the desired salt-forming inorganic or organic acid in a suitable solvent or various combinations of solvents.

The compound of the invention can be synthesized from its constituent amino acids by conventional peptide synthesis techniques, and the additional methods described below. Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

Abbreviations used in the description of the chemistry and in the Examples that follow are:

| | |
|---|---|
| Ac₂O | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| HOBT | 1-Hydroxybenzotriazole hydrate; |
| Et₃N | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

Compound of this invention is prepared by employing the reactions shown in the following Reaction Schemes A–D, in addition to other standard manipulations such as ester hydrolysis, cleavage of protecting groups, etc., as may be known in the literature or exemplified in the experimental procedures. Some key bond-forming and peptide modifying reactions are:

Reaction A: Preparation of a reduced peptide subunit by reductive alkylation of an amine by an aldehyde using sodium cyanoborohydride or other reducing agents.

Reaction B: Alkylation or reductive alkylation of a reduced peptide subunit

Reaction C: Deprotection of the reduced peptide subunit

Reaction D: Coupling of residues to form an amide bond.

These reactions may be employed in a linear sequence to provide the compound of the invention or they may be used to synthesize fragments which are subsequently joined by the reactions described in the Reaction Schemes.

REACTION SCHEME A
Reaction A. Preparation of reduced peptide subunits by reductive alkylation

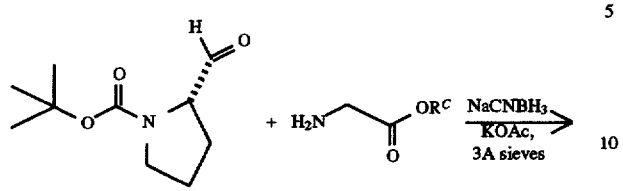

REACTION SCHEME B
Reaction B. Alkylation/reductive alkylation of reduced peptide subunits

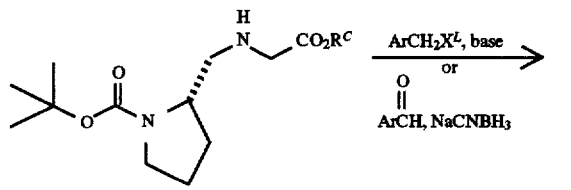

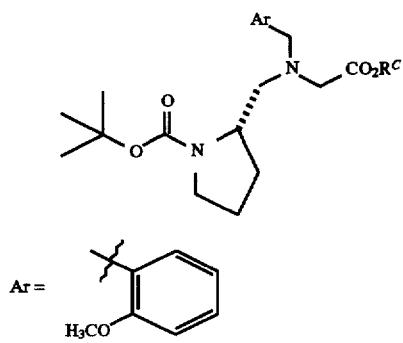

REACTION SCHEME C
Reaction C. Deprotection of reduced peptide subunits

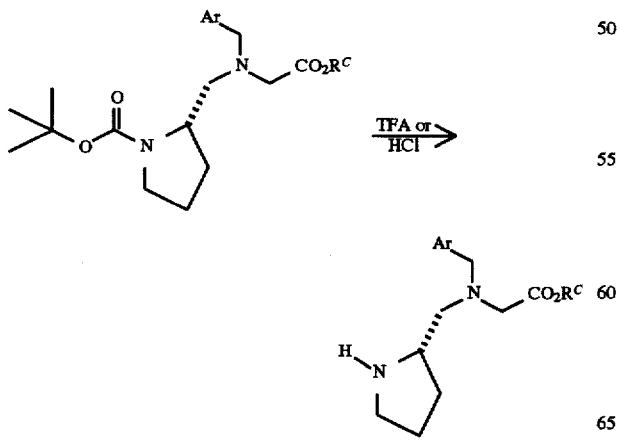

REACTION SCHEME C
Reaction C. Deprotection of reduced peptide subunits

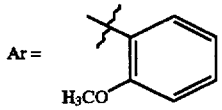

REACTION SCHEME D
Reaction D. Coupling of residues to form an amide bond

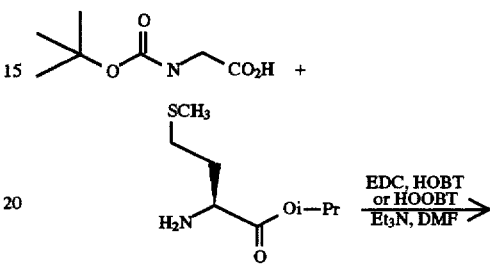

where $R^c$ is a suitable ester protecting group.

Reaction Scheme E illustrates the reaction wherein the non-sulfhydryl-containing moiety at the N-terminus of the compounds of the instant invention is attached to a peptide unit which may be further elaborated to provide the instant compounds. This reaction may be employed following construction of the reduced peptidyl subunit to provide the compound of the invention or it may be used to synthesize fragments which are subsequently joined by the reactions described in Reaction Schemes A–D.

Reaction of 3-imidazolylpropionic acid with the protected dipeptidyl analog intermediate, such as the intermediate whose synthesis is illustrated in Reaction Scheme C, in the presence of condensing reagents such as 1-(3-dimethylaminopropyl)-3-ethylcarbodiimide (EDC) or benzotriazol-1-yloxy-tris(dimethylamino)phosphonium hexafluorophosphate (BOP) leads to acylated products such as I.

REACTION SCHEME E

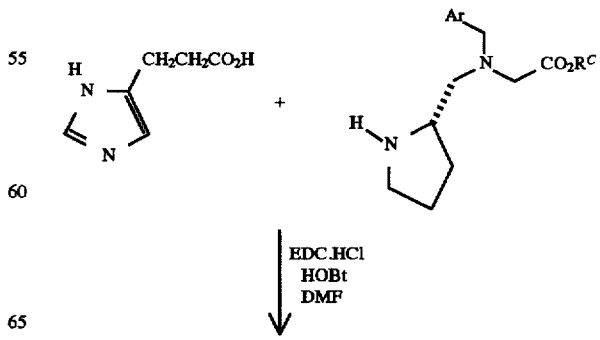

-continued
REACTION SCHEME E

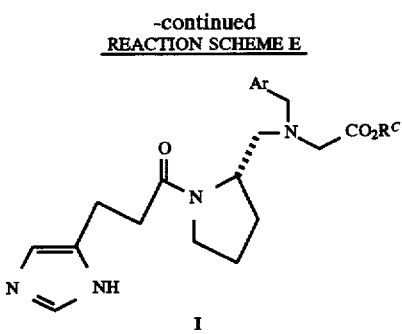

I where $R^c$ is a suitable ester protecting group.

The compound of this invention inhibits Ras farnesyl transferase which catalyzes the first step in the post-translational processing of Ras and the biosynthesis of functional Ras protein. This compound is useful as a pharmaceutical agent for mammals, especially for humans. The compound may be administered to patients for use in the treatment of cancer. Examples of the type of cancer which may be treated with the compound of this invention include, but are not limited to, colorectal carcinoma, exocrine pancreatic carcinoma, and myeloid leukemias.

The compound of this invention is also useful for inhibiting proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compound of the invention to a mammal in need of such treatment. For example, the benign proliferative disorder neurofibromatosis, or tumors in which the Ras is activated due to mutation or overexpression of tyrosine kinase oncogenes (e.g., neu, src, abl, lck, and fyn) may be inhibited by the compound of this invention. Furthermore, arteriosclerosis and diabetic disturbance of blood vessels may be prevented or treated by use of the instant compound to inhibit proliferation of vascular smooth muscle cells.

The compound of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compound can be administered orally or parenterally, including the intravenous, intramuscular, intraperitoneal, subcutaneous, rectal and topical routes of administration.

For oral use of a chemotherapeutic compound according to this invention, the compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compound of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When the compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 50 mg/kg of body weight per day, preferably of between 0.5 mg/kg of body weight to about 40 mg/kg of body weight per day.

The compound of the instant invention is also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compound of the instant invention is a selective inhibitor of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, the potent inhibitor compound of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

Preparation of N-[1-(1H-Imidazol-4-propionyl) pyrrolidin-2(S)-ylmethyl]-N-(2-methoxybenzyl) glycyl-methionine isopropyl ester Step A: Preparation of 2-Methoxybenzlglycine methyl ester 2-Methoxybenzyl alcohol (53.5 g, 0.39 mol) was dissolved in $CH_2Cl_2$ (200 mL), treated with diisopropylethylamine (81 mL, 0.74 mol), cooled to 0° C. with stirring in an ice-$CH_3OH$ bath under Ar, and treated dropwise with methanesulfonyl chloride (33 mL, 0.43 mol). After 0.5 hr, the reaction mixture was left to warm to ambient temperature and stirred for 4 hr. This solution and diisopropylethylamine (202.5 mL, 1.16 mol) were added alternately portionwise with to a slurry of glycine methyl ester hydrochloride (146.5 g, 1.17 mol) in DMF (250 mL) with stirring at 0° C. The reaction mixture was left to stir and warm to room temperature overnight. The DMF was removed under reduced pressure, and the residue was partitioned between EtOAc (1 L) and satd $NaHCO_3$ solution (1 L). The aqueous layer was washed with EtOAc (2×600 mL), the organics combined, washed with brine and dried ($MgSO_4$). Filtration and concentration to dryness gave the title compound after chromatography ($SiO_2$, 1–5% $CH_3OH/CH_2Cl_2$).

Step B: Preparation of N-[(2S)-(t-Butoxycarbonylpyrrolidinylmethyl)-N-(2-methoxybenzyl) glycine methyl ester 2-Methoxybenzylglycine methyl ester (27.4 g, 0.131 mol) was dissolved in 1,2-dichloroethane (500 ml), 3 Å molecular sieves (20 g) were added, and the pH of the reaction mixture adjusted to pH 5 with acetic acid (7.5 mL, 0.131 mol). N-(t-Butoxycarbonyl)-L-prolinal (26.1 g, 0.131 mol) (J. Org. Chem. (1994) 59, [21], 6287–95) was added followed by sodium triacetoxyborohydride (33.2 g, 0.157 mol). The mixture was stirred at ambient temperature for 18 h, filtered through celite and concentrated. The residue was partitioned between EtOAc and sat. $NaHCO_3$ (500 ml/100 ml). The aqueous layer was washed with EtOAc (3×100 ml). The organic layers were combined, dried with $Na_2SO_4$, filtered, and concentrated to give the title compound.

Step C: Preparation of N-[(2S)-(t-Butoxycarbonylpyrrolidinylmethyl-N-(2-methoxybenzyl) glycine N-[(2S)-(t-Butoxycarbonylpyrrolidinylmethyl)-N-(2-methoxybenzyl)glycine methyl ester (7.0 g, 0.018 mol) was dissolved in $CH_3OH$ (150 ml) and 1N NaOH (71 ml, 0.071 mol) was added with cooling in an ice-water bath. The mixture was stirred at ambient temperature for 2 hr, neutralized with 1N HCl (71 ml, 0.071 mol), concentrated to remove the $CH_3OH$, and the residue extracted with EtOAc (3×200 mL). The organic layers were combined, dried with $Mg_2SO_4$, filtered, and concentrated to give the title compound as a foam.

Step D: Preparation of Methionine isopropyl ester hydrochloride

N-(t-Butoxycarbonyl)methionine (25 g, 0.1 mol), isopropyl alcohol (11.8 mL, 0.15 mol), EDC (21.1 g, 0.11 mol), and 4-dimethylaminopyridine (DMAP) (1.22 g, 0.01 mol) were dissolved in $CH_2Cl_2$ (400 mL) with stirring in an ice-water bath. After 2 h the bath was removed, and the solution was left to stir o.n. at RT. The reaction mixture was concentrated to dryness, then partitioned between EtOAc and $H_2O$, the aqueous layer washed with EtOAc (2×50 mL), the organics combined, washed with $NaHCO_3$ soln, brine, and dried ($Na_2SO_4$). Filtration and concentration to dryness gave a yellow oil after chromatography (flash silica gel column, hexane: EtOAc, 6:1 to 5:1).

N-(t-Butoxycarbonyl)methionine isopropyl ester (20.5 g, 0.07 mol) was dissolved in EtOAc (200 mL) with stirring and cooling to −20° C. in a dry ice- acetone bath. HCl gas was bubbled into the solution for 10 min, the flask was stoppered and stirred for 1 h. Tlc (EtOAc: hexane, 1:3) indicates loss of starting material. Argon was bubbled through the soln for 5 min, then it was concentrated to dryness to give the title compound as a white solid.

Step E: Preparation of N-[(2S)-(t-Butoxycarbonylpyrrolidinylmethyl)-N-(2-methoxybenzyl) glycyl-methionine isopropyl ester N-[(2S)-(t-Butoxycarbonylpyrrolidinylmethyl)-N-(2-methoxybenzyl)glycine (from step C) (5.98 g, 0.0158 mol), dissolved in $CH_2Cl_2$ (100 mL), was treated with HOBT (2.57 g, 0.019 mol), EDC (4.54 g, 0.024 mol), and methionine isopropyl ester hydrochloride (4.33 g, 0.019 mol). The pH was adjusted to 7.5 with $Et_3N$ (8.81 mL, 0.063 mol) and the mixture was stirred at ambient temperature for 18 h. The mixture was diluted with EtOAc (150 mL) and washed sequentially with 10% citric acid soln, saturated $NaHCO_3$ solution, brine, and dried ($MgSO_4$). Filtration and concentration to dryness gave the title compound as a thick oil. This was used without further purification.

Step F: Preparation of N-((2S)-Pyrrolidinylmethyl)-N-(2-methoxybenzyl)-glycyl-methionine isopropyl ester bis hydrochloride N-[(2S)-(t-Butoxycarbonylpyrrolidinylmethyl)-N-(2-methoxybenzyl)glycyl-methionine isopropyl ester (0.85 g, 1.54 mmol) was dissolved in EtOAc (25 mL) and cooled to 0° C. HCl was bubbled through the mixture until the soln was saturated, and it was stoppered and stirred for 3 hr. Argon was bubbled through the mixture to remove excess HCl and the mixture was then concentrated to give the title compound.

Step G: Preparation of N-[1-(1H-Imidazol-4-propionyl) pyrrolidin-2(S)-ylmethyl]-N-(2-methoxybenzyl) glycyl-methionine isopropyl ester N-((2S)-Pyrrolidinylmethyl)-N-(2-methoxybenzyl)glycyl methionine isopropyl ester bis hydrochloride (0.800 g, 1.53 mmol), dissolved in DMF (30 mL), was treated with 1H-imidazol-4-propionic acid (0.43 g, 3.05 mmol) (prepared by catalytic hydrogenation of urocanic acid in 20% acetic acid with Pd on carbon), and BOP reagent (1.35 g, 3.05 mmol). The pH was adjusted to 7.5 with N-methlmorpholine (0.756 mL, 6.89 mmol), and the mixture was stirred at ambient temperature for 18 h. The mixture was concentrated to dryness, diluted with EtOAc (100 mL), washed with 5% $Na_2CO_3$ solution, brine, and dried ($MgSO_4$). Filtration and concentration to dryness gave an oil which was purified by chromatography (silica gel, 95:5 $CH_2Cl_2$/MeOH) to give the title compound as a foam.

$^1$H NMR ($CD_3OD$); δ7.58 (d, 1H, J=1 Hz), 7.25–7.31 (m, 2H), 6.89–7.00 (m, 2H), 6.81 (s, 1H), 5.00–5.06 (m, 1H), 4.49–4.56 (m, 1H), 4.23–4.30 (m, 1H), 3.91 (d, 1H, J=13 Hz), 3.86 (s, 3H), 3.54 (d, 1H, J=13Hz), 3.30–3.41 (m, 2H), 3.36 (d, 1H, J=17 Hz), 3.15 (d, 1H, J=17 Hz), 2.85–2.92 (m, 2H), 2.56–2.77 (m, 3H), 2.30–2.45 (m, 3H), 2.05–2.17 (m, 1H), 2.04 (s, 3H), 1.69–1.86 (m, 5H), 1.24 (d, 6H, J=6 Hz).

Anal. calculated for $C_{29}H_{43}N_5O_5S \cdot 0.6 H_2O$: C, 59.59; H, 7.62; N, 11.98; Found: C, 59.58; H, 7.43; N, 12.02.

Example 2

Preparation of N-[1-(1H-Imidazol-4-propionyl) pyrrolidin-2(S)-ylmethyl]-N-(2-methoxybenzyl) glycyl-methionine Step A: Preparation of N-(t-Butoxycarbonylpyrrolidin-2 (S)-ylmethyl) glycine methyl ester N-(t-Butoxycarbonyl)-L-prolinal (9.16 g, 0.046 mol) and glycine methyl ester hydrochloride salt (5.78 g, 0.046 mol) were dissolved in MeOH (180 mL) at 0° C. under nitrogen, treated with sodium cyanoborohydride (4.34 g, 0.069 mol), and stirred for 18 h. The mixture was concentrated, and the residue was partitioned between EtOAc (100 mL) and satd aq $NaHCO_3$ soln (100 mL). The basic layer was washed with EtOAc (2×50 mL), the organics combined washed with brine, and dried over $Na_2SO_4$. Filtration and concentration to dryness gave the title compound as a pale yellow oil. $^1H$ NMR ($CDCl_3$) δ3.7–3.9 (m, 1H), 3.72 (s, 3H), 3.43 (s, 2H), 3.33 (s, 2H), 2.7–2.9 (m, 1H), 2.5–2.65 (m, 1H), 1.75–2.0 (m, 4H), 1.47 (s, 9H).

Step B: Preparation of N-(t-Butoxycarbonylpyrrolidin-2(S) -ylmethyl)-N-(2-methoxybenzyl) glycine methyl ester N-(t-Butoxycarbonylpyrrolidin-(2S)-ylmethyl) glycine methyl ester (3.0 g, 0.011 mol) was dissolved in 1,2-dichloroethane (70 ml) and 3A molecular sieves (3 g) were added followed by o-anisaldehyde (1.3 ml, 0.011 mol) and sodium triacetoxyborohydride (3.27 g, 0.015 mol). The mixture was stirred at ambient temperature for 16 h, filtered through Celite and concentrated. The residue was partitioned between EtOAc and sat. $NaHCO_3$ (100 ml/25 ml). The aqueous layer was washed with EtOAc (3×50 ml). The organic layers were combined, dried with $MgSO_4$, filtered, and concentrated to give the crude product which was purified by chromatography (silica gel 15% EtOAc/hexane) to give the title compound.

Step C: Preparation of N-(t-Butoxycarbonylpyrrolidin-2(S) -ylmethyl)-N-(2-methoxybenzyl)glycine N-(t-Butoxycarbonylpyrrolidin-(2S)-ylmethyl)-N-(2-methoxybenzyl)glycine methyl ester (1.83 g, 4.65 mmol) was dissolved in $CH_3OH$ (30 ml) with cooling in an ice-water bath and 1N NaOH (18.6 ml, 18.6 mmol) was added. The bath was removed, and the mixture was stirred at ambient temperature for 2 h, then neutralized with 1N HCl (18.6 ml). The mixture was concentrated to remove the $CH_3OH$, and the residue extracted with EtOAc (3×100 ml). The organic layers were combined, washed with brine, and dried ($MgSO_4$), filtered, and concentrated to give the title compound.

Step D: Preparation of N-(t-Butoxycarbonylpyrrolidin-2(S) -ylmethyl-N-(2-methoxybenzyl)glycine-methionine methyl ester N-(t-Butoxycarbonylpyrrolidin-(2S)-ylmethyl)-N-(2-methoxybenzyl) glycine (0.65 g, 1.72 mmol), dissolved in $CH_2Cl_2$ (10 mL), was treated with HOBT (0.278 g, 2.06 mmol), EDC (0.494 g, 2.58 mmol), and methionine methyl ester hydrochloride (0.412 g, 2.06 mmol). The pH was adjusted to 7.5 with $Et_3N$ (0.958 mL, 6.87 mmol) and the mixture was stirred at ambient temperature for 2 h. EtOAc (150 mL) was added, and the mixture was washed with 10% citric acid, $H_2O$, saturated $NaHCO_3$ solution, brine, and dried ($MgSO_4$), filtered, and concentrated to give the title compound.

Step E: Preparation of N-(Pyrrolidin-(2S)-ylmethyl)-N-(2-methoxybenzyl)-glycyl-methionine methyl ester hydrochloride N-(t-Butoxycarbonylpyrrolidin-(2S)-ylmethyl)-N-(2-methoxybenzyl)-glycyl-methionine methyl ester (0.852 g, 1.63 mmol) was dissolved in EtOAc (10 mL) and cooled to 0° C. HCl was bubbled through the mixture until saturation, and the solution stirred at 0° C. for 1 hr. Argon was bubbled through the mixture to remove excess HCl and the mixture was concentrated to give the title compound.

Step F: Preparation of N-[1-(1H-Imidazol-4-propionyl) pyrrolidin-2(S)-ylmethyl]-N-(2-methoxybenzyl)glycyl-methionine methyl ester hydrochloride N-(Pyrrolidin-2(S)-ylmethyl)-N-(2-methoxybenzyl)-glycyl-methionine methyl ester hydrochloride (0.200 g, 0.407 mmol), imidazolepropionic acid (0.114 g, 0.82 mmol), BOP reagent (0.365 g, 0.82 mmol), and N-methylmorpholine (0.20 mL, 1.63 mmol) were dissolved in dry DMF (10 mL) and stirred under Ar for 18 h. The mixture was concentrated in vacuo and the residue partitioned between EtOAc and 5% $Na_2CO_3$ solution. The aqueous layer was back extracted with EtOAc, the organics combined, washed with brine, and dried ($MgSO_4$). Filtration and concentration to dryness gave the crude compound as an oil which was purified by RP HPLC using a 0.1% TFA in $CH_3CN$: 0.1% TFA in $H_2O$ gradient (5:95 to 95:5) followed by lyophilization and conversion to the HCl salt. FAB MS 546 (M+1).

Anal. Calcd for $C_{27}H_{39}N_5O_5S.2$ HCl.1.9 $CF_3CO_2H.0.1$ $H_2O$: C, 44.19;H, 5.19; N, 8.37; Found: C, 44.17;H, 5.21; N, 8.21.

Step G: Preparation of N-[1-(1H-Imidazol-4-propionyl) pyrrolidin-2(S)-ylmethyl]-N-(2-methoxybenzyl)glycyl-methionine bis trifluoroacetate salt N-[1-(1H-Imidazol-4-propiony)pyrrolidin-2(S)-ylmethyl]-N-(2-methoxybenzyl)glycyl-methionine methyl ester (0.020 g, 0.024 mmol) was dissolved in THF (1 mL) with cooling in an ice bath. 1N NaOH (0.144 mL, 0.144 mmol) was added, the bath was removed, and the mixture was stirred for 2 h. The mixture was cooled in an ice bath and treated with 1N HCl (0.144 mL, 0.144 mmol), and the solution purified on a RP HPLC VYDAC column (0.1% TFA in $CH_3CN$: 0.1% TFA in $H_2O$, 5:95 to 95:5 gradient) and lyophilized to give the title compound.

$^1H$ NMR ($CD_3OD$) δ8.74 (d, 1H, J=1.5 Hz), 7.85 (d, 2H, J=7 Hz), 7.76 (t, 1H, J=7 Hz), 7.56–7.66 (m, 1H), 7.35 (s, 1H), 4.37–4.58 (m, 3H), 3.70–3.83 (m, 1H), 3.46–3.60 (m, 2H), 3.30 (s, 3H), 3.12–3.35 (m, 4H), 3.02–3.90 (m, 2H), 2.70–2.85 (m, 2H), 2.44–2.60 (m, 2H), 2.05–2.20 (m, 2H), 2.07 (s, 3H), 1.91–2.02 (m, 3H), 1.82–1.90 (m, 1H).

Anal. Calcd for $C_{26}H_{37}N_5O_5S.2.9$ $CF_3CO_2H.1.1$ $H_2O$: C, 43.30; H, 4.81; N, 7.94; Found: C, 43.28; H, 4.75; N, 7.98.

Example 3

In vitro inhibition of ras farnesyl transferase

Assays of farnesyl-protein transferase.

Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., PNAS U.S.A. 86:6630–6634 (1989), respectively. Bovine FPTase was assayed in a volume of 100 µl containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3H$]-farnesyl diphosphate ([$^3H$]-FPP; 740 CBq/mmol, New England Nuclear), 650 nM Ras-CVLS and 10 µg/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 µM ZnCl$_2$ and 100 nM Ras-CVIM were added to the reaction mixture. Reactions were performed for 30 min., stopped with 100 µl of 30% (v/v) trichloroacetic acid (TCA) in ethanol and processed as described above for the bovine enzyme.

The compound described in Example 2 was tested for inhibitory activity against human FPTase by the assay described above and was found to have IC$_{50}$ of <10 µM.

Example 4

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 5

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 6

In vivo pharmacodynamic effects of farnesyl-protein transferase inhibitors in mammalian white blood cells The test mammal (beagle, Cynomolgus monkey, Rhesus monkey or African green monkey) is dosed by an IV, PO or suppository dose of a given concentration of drug in a suitable vehicle, such as IV:5% EtOH/citrate buffered saline, PO:50 mmol citric acid in water and suppository: 17.7% compound, 38% hydrous lactose; 44.3% PEG 8000.

Following drug dosing, the animals are bled at times t=0, 5 mins., 15 mins., 30 mins., 60 mins., 90 mins., 180 mins.(3 hours), 270 mins. (4.5 hours), 360 mins. (6 hours) and 1440 mins. (24 hours) by withdrawing 3 mL of blood into a sodium heparin vacutainer tube and placing the drawn blood immediately on ice. The vacutainer tubes are then spun at 2800 rpm in a table top centrifuge for 5 minutes at 4 degrees. Following the spin, the upper plasma layer is withdrawn from the vacutainer tube leaving an ⅛" of plasma on top of the blood pellet. The vacutainer tubes and plasma tubes are then put into dry ice for a quick freeze and once frozen, the samples are stored at –70° degrees.

For evaluation of the white blood cells, the frozen vacutainer tube is broken at the bottom utilizing a triangular metal file, and the frozen pellet of blood is removed (prior to breaking the tube it can warmed slightly in a 30° bath taking precautions not to melt the pellet). A razor/scalpel is used to chop off the top ¼" of the blood pellet (this is where the white blood cell layer is located).

The pellet layer is then put into 10 mL of cold PBS (15 mL conical centrifuge tube) and the mixture is allowed to nutate until the red blood cell layer is solublized leaving the white blood cell layer. When the red blood cell layer is solublized, the conical tube is placed into ice until all samples are solublized, then nutated in a cold room for approximately 10 mins. The tubes are then spun for 5 mins. at 2800 rpm and 4 degrees.

The samples are aspirated utilizing a glass pipette that has a p200 pipette tip on its end connected to the house vacuum with two special traps to collect the waste. Care is taken to leave the white blood cell pellet in the tube. Another 10 mL of cold PBS is added to each conical tube and the pellet rinsed carefully to remove any residual red blood cells. The tube is then nutated in the cold room for 10 mins. and centrifuged for 5 mins. at 2800 rpm, 4°. The sample is then aspirated, carefully, and centrifuged again for another 4 mins. A final aspiration is then done to remove all excess liquid waste.

80 µL of 1× lysis buffer (described below) is added to the sample and the sample is then sonicated for 15–20 seconds in the cold room (after each sample is sonicated, a wet paper towel is used to wipe off the probe and then a dry towel to dry probe). The sample is spun at 2800 rpm for 5 mins. in a table-top centrifuge and the supernatent is removed and put into a pre-labeled eppendorf tube. That tube is spun in a microfuge in the cold room at high speed for 8 mins.

The lysate is transferred to a clear eppendorf tube for color observations. (If the sample is clearly dark red or has color there may be contamination by red blood cells, therefore affecting the Bradford concentrations. It is be important to know the presence of color when working up the data later).

A portion of the lysate 63 µL is transferred to a farnesylation reaction tube (1.7 mL eppendorfs tube) and the lysate is preincubated for 1–2 mins. at 30°. The reaction is then initiated by adding 7 µL of "master mix" (described below) to the tube. When the master mix is added, the mixture is pipetted up and down vigorously into the lysate, then 10 µL of the mixture is removed (for t=0) and quenched into 2 mL 10% HCl/EtOH.

Once the farnesylation reactions are started it is only necessary to remove 10 µL at the desired time points and quench. Time points of 1 min., 2 mins., 3 mins., and 4 mins. are typically chosen. This process is then repeated for all the samples. Three samples may be concurrently evaluated using this procedure by staggering the initiation of each reaction at twenty second intervals.

After the reaction has been quenched, the product is collected on a filter by the cell harvester method. The filter is then washed and radio-counted. A Bradford protein assay is then performed on all lysate samples and the data is calculated to obtain a percent inhibition of farnesyl-protein transferase, normalized for total protein, compared to farnesyl-protein transferase activity in the white blood cells of the same animal, prior to treatment. The compound of the instant invention was analyzed in this assay.

10× BUFFER 500 mM Na Hepes pH 7.5
50 mM MgCl$_2$
50 mM DTT
100 uM ZnCl$_2$
1% PEG (15–20 k)

1× LYSIS BUFFER

1:10 Dilution of 10× buffer
Aprotinin 10 ug/ml
Leupeptin 2 ug/ml
Antipain 2 ug/ml
AEBSF 10 ug/ml
NaVo3

MASTER MIX 100 nM $^3$H-FPP Final/70 µL rxn
100 nM CVIM Final/70 µL rxn
7 µL 10× buffer/70 µL rxn

What is claimed is:

1. A compound which inhibits farnesyl-protein transferase which is:

N-[1-(1H-Imidazol-4-propionyl) pyrrolidin-2(S)-ylmethyl]-N-(2-methoxybenzyl)glycyl-methionine isopropyl ester

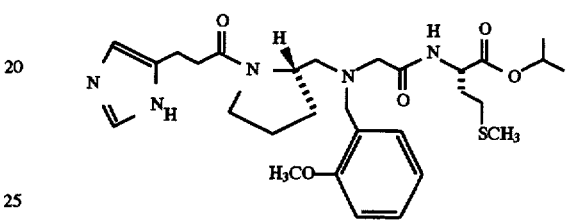

or a pharmaceutically acceptable salt thereof.

2. A pharmaceutical composition comprising a pharmaceutical carrier, and dispersed therein, a therapeutically effective amount of a compound of claim 1.

3. A method for inhibiting farnesyl-protein transferase which comprises administering to a mammal in need thereof a therapeutically effective amount of the composition of claim 2.

4. A method for treating cancer which comprises administering to a mammal in need thereof a therapeutically effective amount of a composition of claim 2.

* * * * *

UNITED STATES PATENT AND TRADEMARK OFFICE
CERTIFICATE OF CORRECTION

PATENT NO. : 5,703,241
DATED : Dec. 30, 1997
INVENTOR(S) : S. Jane deSolms, et al It is certified that error appears in the above-identified patent and that said Letters Patent is hereby corrected as shown below:

Title page, insert the following:

--Related U.S. Application Data
[60] Provisional application No. 60/007,001, Oct. 16, 1995--.

Column 1, line 2, insert the following:

--CROSS REFERENCE TO RELATED APPLICATION
Reference is made to and priority claimed from U.S. Provisional application Ser. No. US 60/007,001, filed Oct. 16, 1995, entitled INHIBITOR OF FARNESYL-PROTEIN TRANSFERASE.--

Signed and Sealed this

Second Day of February, 1999

*Attest:*

*Attesting Officer*

*Acting Commissioner of Patents and Trademarks*